(12) United States Patent
Schiffman et al.

(10) Patent No.: US 8,864,694 B2
(45) Date of Patent: Oct. 21, 2014

(54) BRACE

(76) Inventors: Eric Schiffman, St. Paul, MN (US); Thomas Michael Speidel, Minneapolis, MN (US)

( * ) Notice: Subject to any disclaimer, the term of this patent is extended or adjusted under 35 U.S.C. 154(b) by 138 days.

(21) Appl. No.: 13/457,376

(22) Filed: Apr. 26, 2012

(65) Prior Publication Data

US 2013/0289460 A1 Oct. 31, 2013

(51) Int. Cl.
*A61F 5/00* (2006.01)

(52) U.S. Cl.
USPC .......................................................... 602/18

(58) Field of Classification Search
CPC ........... A61F 5/01; A61F 5/0102; A61F 5/04; A61F 5/055; A61F 5/058; A61F 5/05883; A61G 13/02; A61G 13/12; A61G 13/121; A47C 20/00
USPC ........ 602/5, 16–19, 32; 128/97.1, 103.1, 846, 128/869, 870; 5/621, 622, 637
See application file for complete search history.

(56) References Cited

U.S. PATENT DOCUMENTS

| 2,223,276 | A | * | 11/1940 | Ward | 602/18 |
| 2,735,424 | A | * | 2/1956 | Benjamin | 602/17 |
| 2,820,455 | A | * | 1/1958 | Hall | 602/18 |
| 2,904,040 | A | * | 9/1959 | Hale | 602/18 |
| 4,628,913 | A | * | 12/1986 | Lerman | 602/18 |
| 5,201,702 | A | * | 4/1993 | Mars | 602/17 |
| 5,208,928 | A | * | 5/1993 | Kuck et al. | 5/608 |
| 5,531,669 | A | * | 7/1996 | Varnau | 602/18 |
| 7,789,843 | B2 | * | 9/2010 | Ray | 602/18 |
| 8,001,633 | B2 | * | 8/2011 | Swain, Jr. | 5/621 |
| 8,057,415 | B2 | * | 11/2011 | Hipp et al. | 602/18 |
| 8,529,482 | B2 | * | 9/2013 | Giontella | 602/18 |
| 2006/0217648 | A1 | * | 9/2006 | Rogachevsky | 602/20 |
| 2009/0187129 | A1 | * | 7/2009 | Ben-Galim et al. | 602/18 |

* cited by examiner

*Primary Examiner* — Patricia Bianco
*Assistant Examiner* — Raymond E Harris
(74) *Attorney, Agent, or Firm* — Roger L. Belfay

(57) ABSTRACT

The brace includes: a chest plate; a chin support; a rod having a top surface, the rod adjustably attached to the chest plate; and an adjustable linkage connected to the top surface and to the chin support. The brace is used to immobilize a Patient's chin relative to The Patient's spinal column, or The Patient's chest, or both when the Patient's chin is placed upon the chin support.

8 Claims, 10 Drawing Sheets

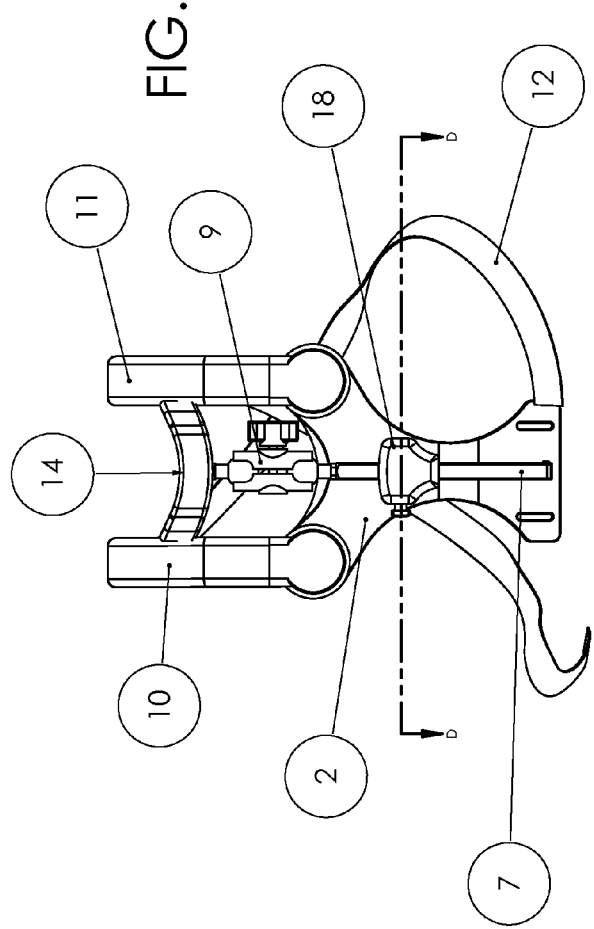
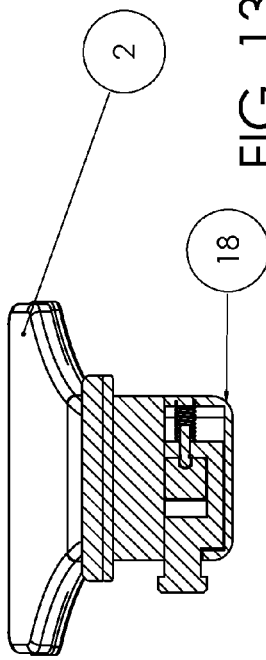
FIG. 12
FIG. 13

US 8,864,694 B2

BRACE

CROSS REFERENCE TO RELATED APPLICATIONS

There are no applications related to this application.

STATEMENT REGARDING FEDERALLY SPONSORED RESEARCH OR DEVELOPMENT

No invention claimed in this application was made under Federally sponsored research or development.

THE NAMES OF THE PARTIES TO A JOINT RESEARCH AGREEMENT

Not Applicable

REFERENCE TO A SEQUENCE LISTING

Not Applicable

BACKGROUND OF THE INVENTION

1. Field of the Invention

The Brace is a device for immobilizing the chin of a patient requiring medical treatment. As such this invention relates to the filed of medical and dental apparatuses used to restrict patient movement where such movement would be risky or counterproductive to the procedure or procedure which the patient will be undergoing.

2. Description of Related Art

Braces are known in the art which support the chin rigidly to a chest harness of other reference point. Typically these devices provide for one degree of freedom in the adjustment of the distance from the patient's chest to the patient's chin. Utility U.S. Pat. No. 3,724,452 to Nitschke, U.S. Pat. No. 7,549,970 to Tweardy, U.S. Pat. Nos. 6,267,741 and 6,368,295 to Lerman, and U.S. Pat. No. 5,054,475 to Calabrese et al are typical of this class of brace. It is an object of the present invention to provide additional degrees of freedom in the adjustment of the patient's chin relative to the said patient's chest.

Braces are also known in the art which support the chin rigidly relative to the body by providing a head restraint which is rigidly fixed to a harness attached at the patient's back. Utility U.S. Pat. No. 5,409,450 to Donelson, U.S. Pat. No. 7,549,970 to Tweardy, U.S. Pat. Nos. 6,267,741 and 6,368,295 to Lerman, and U.S. Pat. No. 5,054,475 to Calabrese et al are typical of this class of brace. It is the object of this invention to provide a brace which can be used by a patient while sitting in a chair.

BRIEF SUMMARY OF THE INVENTION

The brace comprises: a chest plate; a chin support for supporting a Patient's chin in a fixed position relative to said Patient's chest; a rod having a top surface, said rod adjustably attached to said chest plate; and an adjustable linkage connected to said top surface and to said chin support. The brace is used to immobilize a Patient's chin relative to The Patient's spinal column, or The Patient's chest, or both when said Patient's chin is placed upon the chin support.

BRIEF DESCRIPTION OF THE SEVERAL VIEWS OF THE DRAWINGS

FIG. 12 is a front view of the brace.
FIG. 13 is a detail view of the brace.

DETAILED DESCRIPTION OF THE INVENTION

Figure 1:
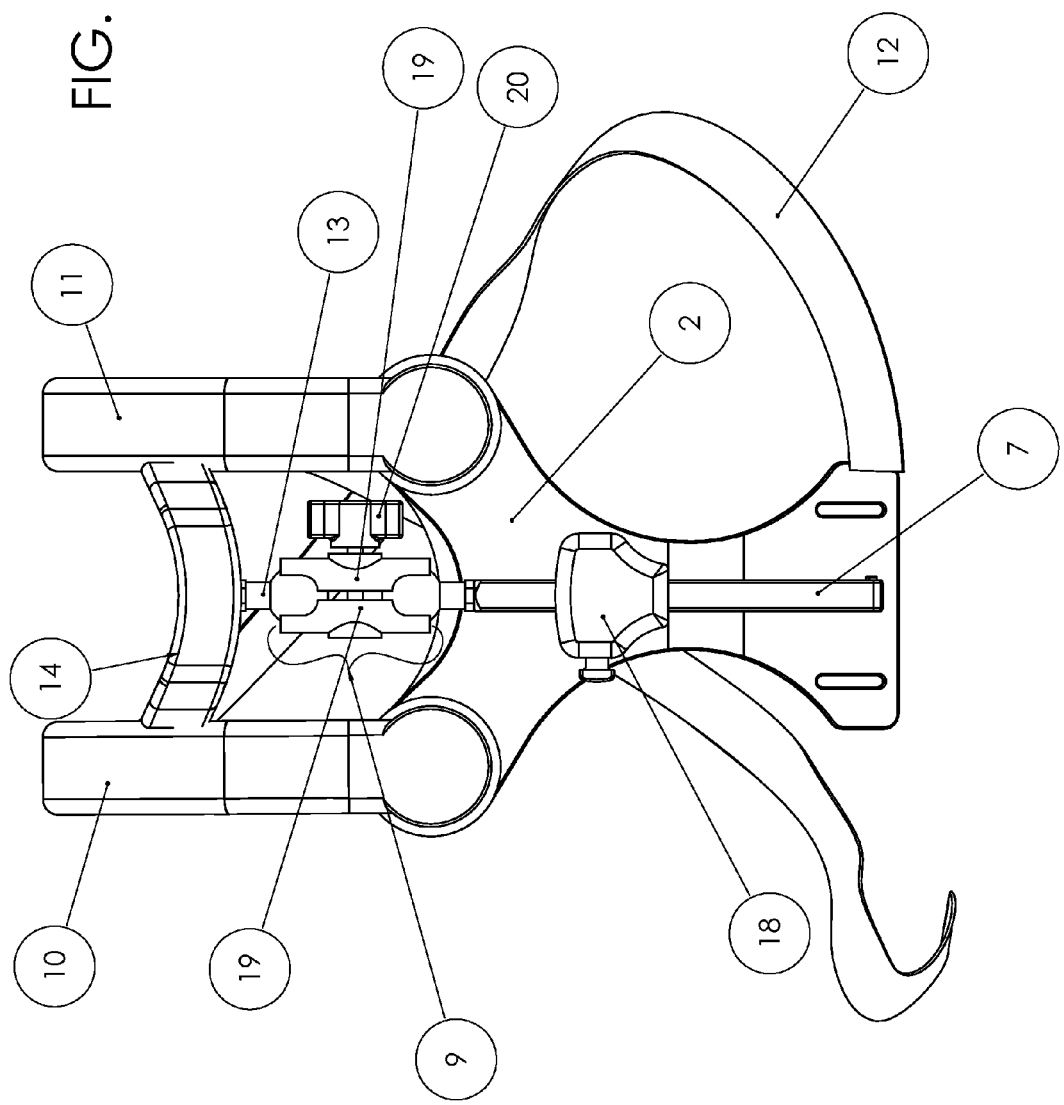
FIG. 1 is a front view of the brace.
Figure 2:
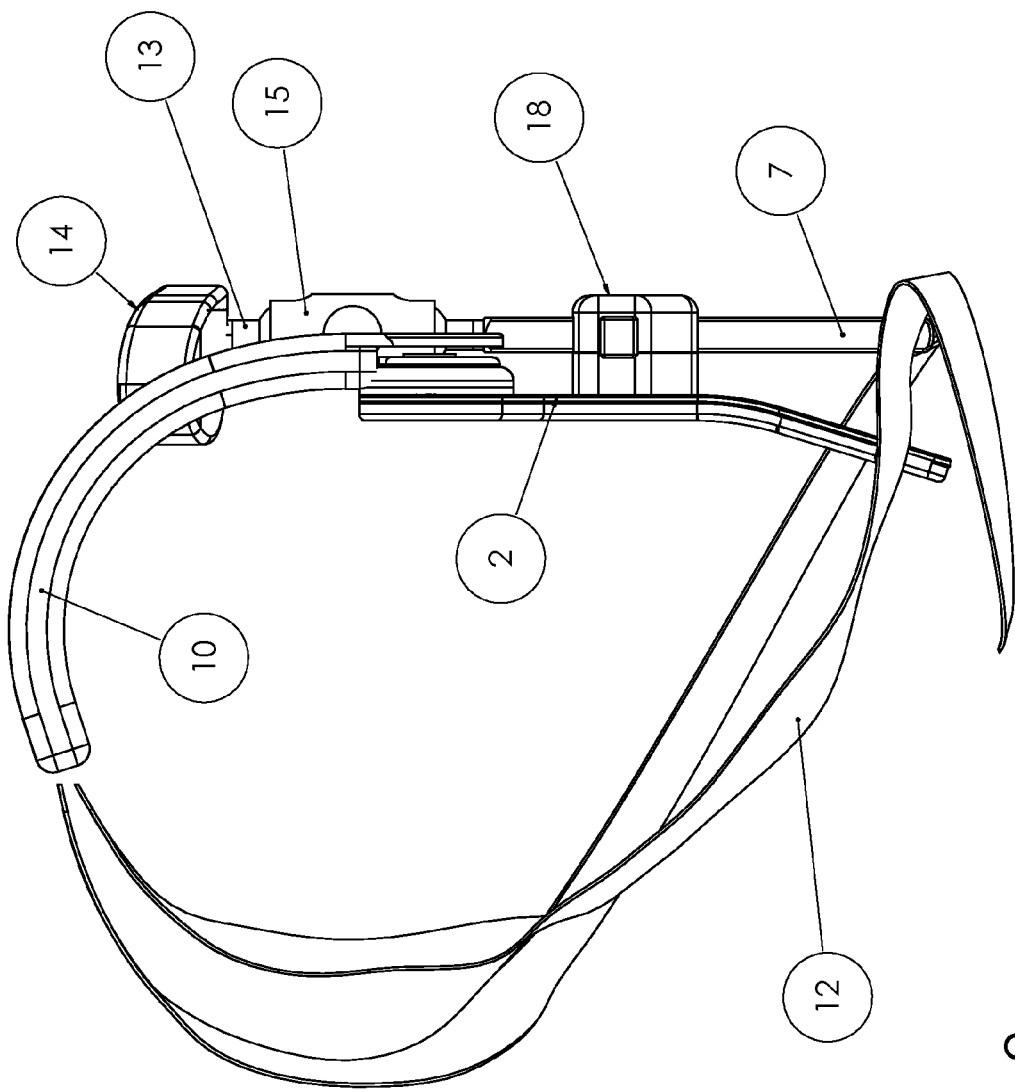
FIG. 2 is a side view of the brace.
Figure 3:
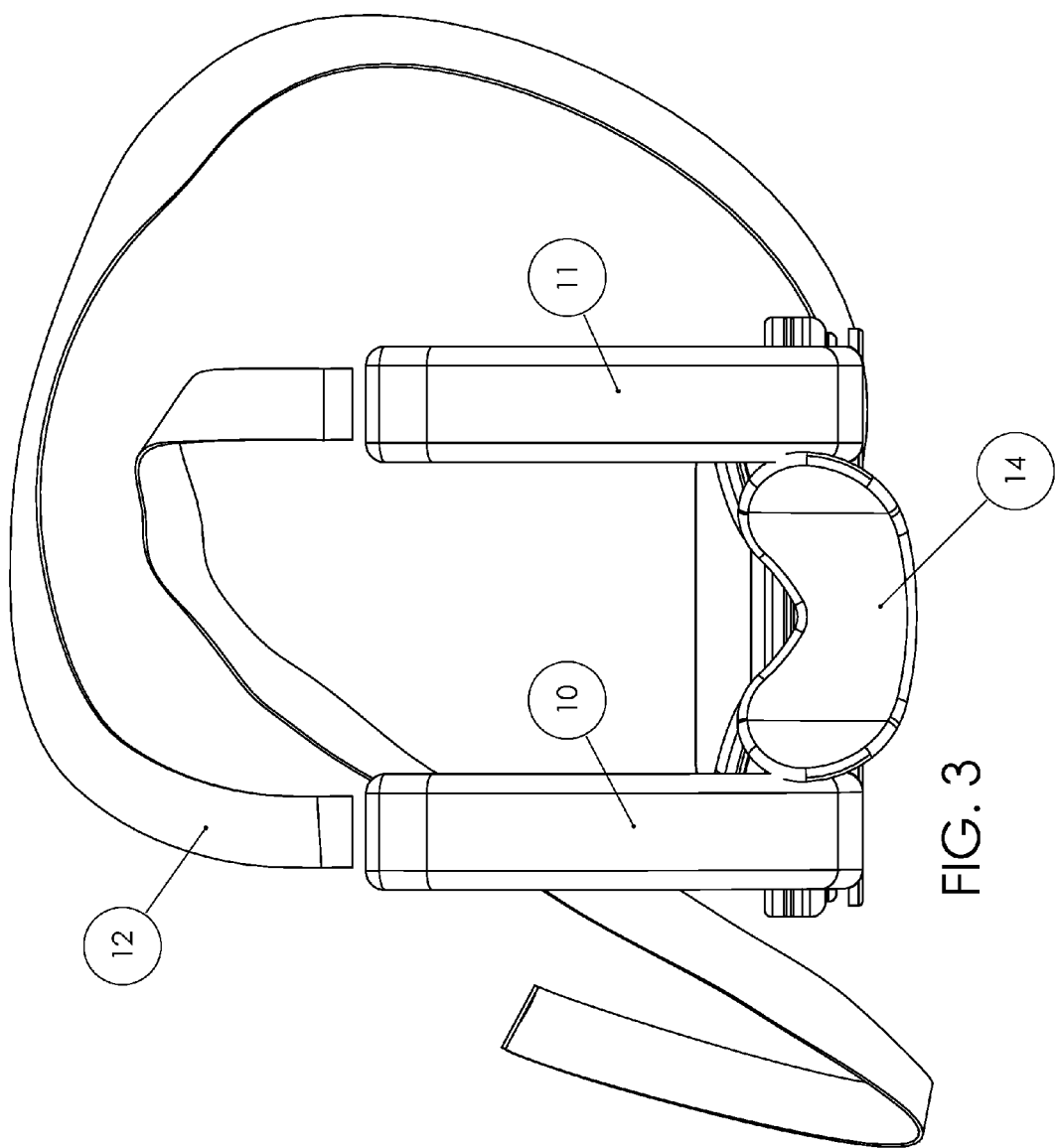
FIG. 3 is a top of the brace.

The brace 1 comprises: a chest plate 2; a chin support for supporting a Patient's chin 4 in a fixed position relative to said Patient's chest; a rod 7 having a top surface 8, said rod 7 adjustably attached to said chest plate 2; and an adjustable linkage 15 connected to said top surface 8 and to said chin support. The brace 1 is used to immobilize a Patient's chin 4 relative to The Patient's The Patient's chest when said Patient's chin 4 is placed upon the chin support.

The chest plate 2 is a base formed to fit comfortably against The Patient's chest and is formed of any plastic, metal, or other material having sufficient strength to support the chin support when used to immobilize said Patient's chin 4. The chest plate 2 is also provided with a left shoulder brace 10 and a right shoulder brace 11. Each shoulder brace is provided with one or more adjustable straps 12 attached to the bottom portion of the chest plate 2. The shoulder braces and straps secure the chest plate 2 to the Patient's chest. It is appreciated that additional braces and straps are contemplated as within the present invention.

The chin support is a metal or plastic frame which includes a post 13 attached to an adjustable linkage 9 and a pad 14. In another embodiment the adjustable linkage 15 includes a post 13 attached to the chin support. In both embodiments the post 13 may be threaded to match a threaded hole to achieve the desired connection. Alternatively, the post may be attached to the chin support or post 13 by welding or by a suitable adhesive. When in use the pad 14 is placed in contact with the Patient's chin 4.

The rod 7 has a top surface 8 attached to the adjustable linkage 15 and is slideably attached, and may be rotatably attached, to the chest plate 2 to permit adjustment of the position of the chin support relative to the Patient's chest. The rod 7 is of any desired cross section but a circular cross section facilitates rotational attachment to the chest plate 2.

Figure 4:
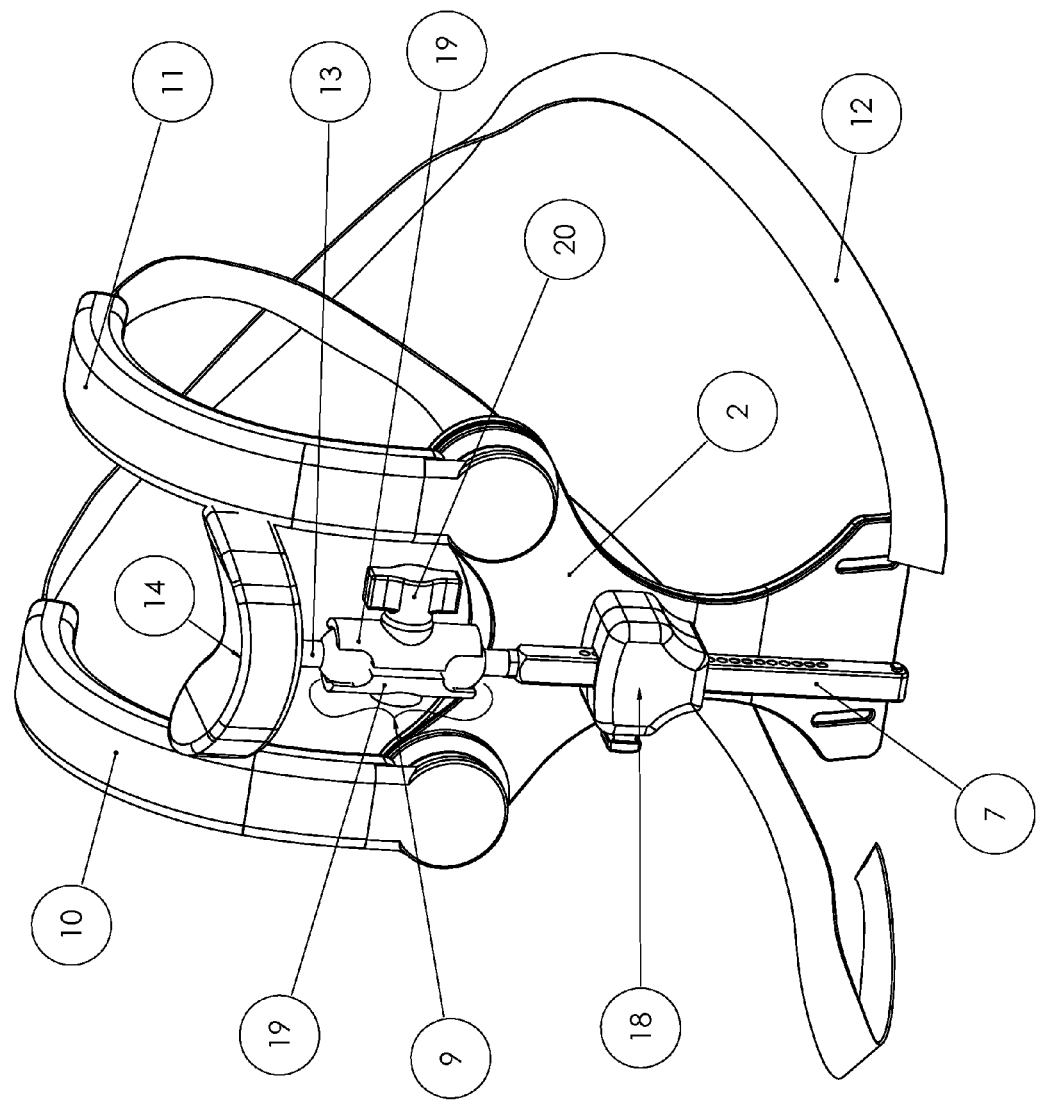
FIG. 4 is an isometric view of the brace.
Figure 5:
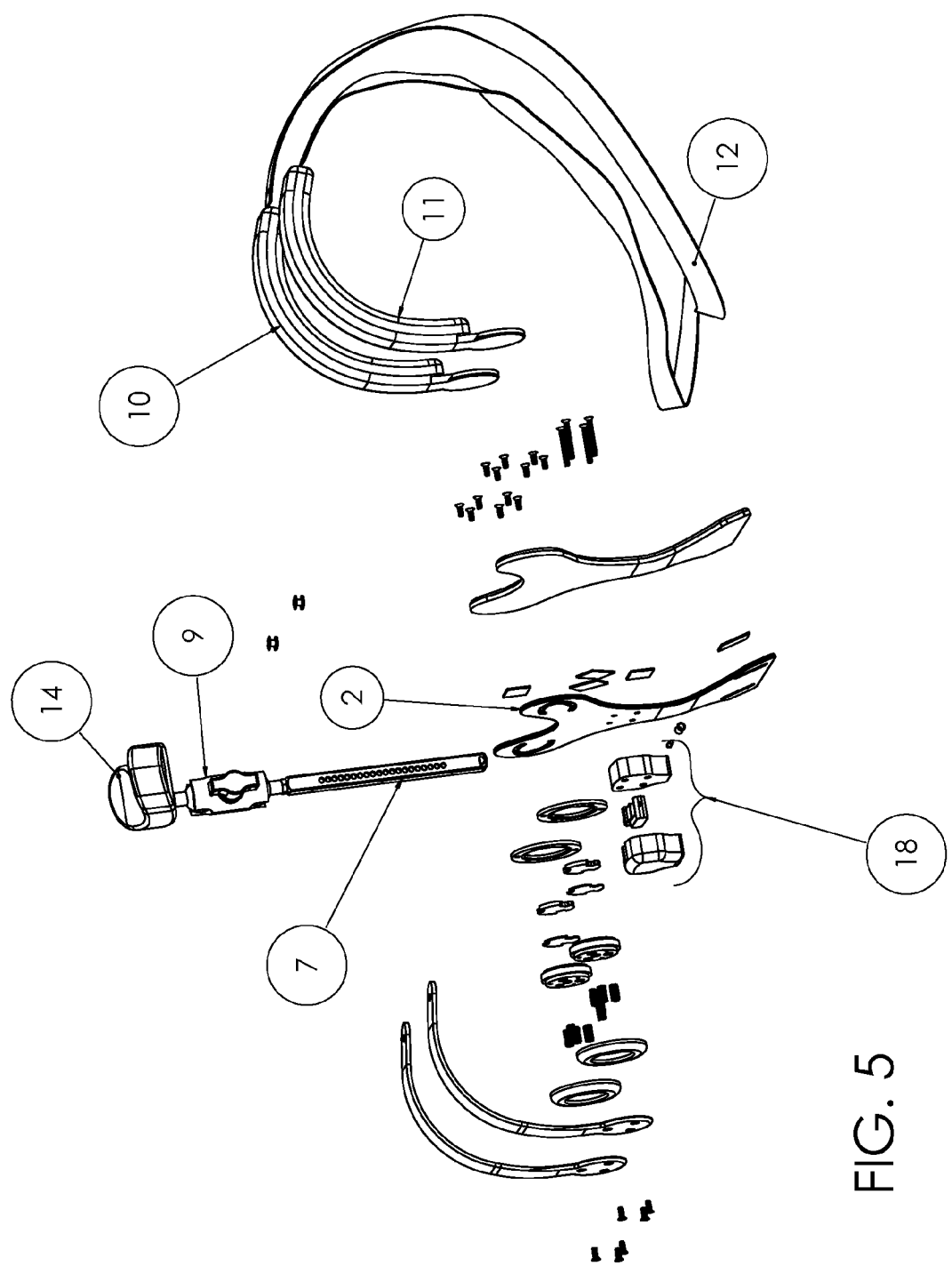
FIG. 5 is an exploded view of the brace.
Figure 6:
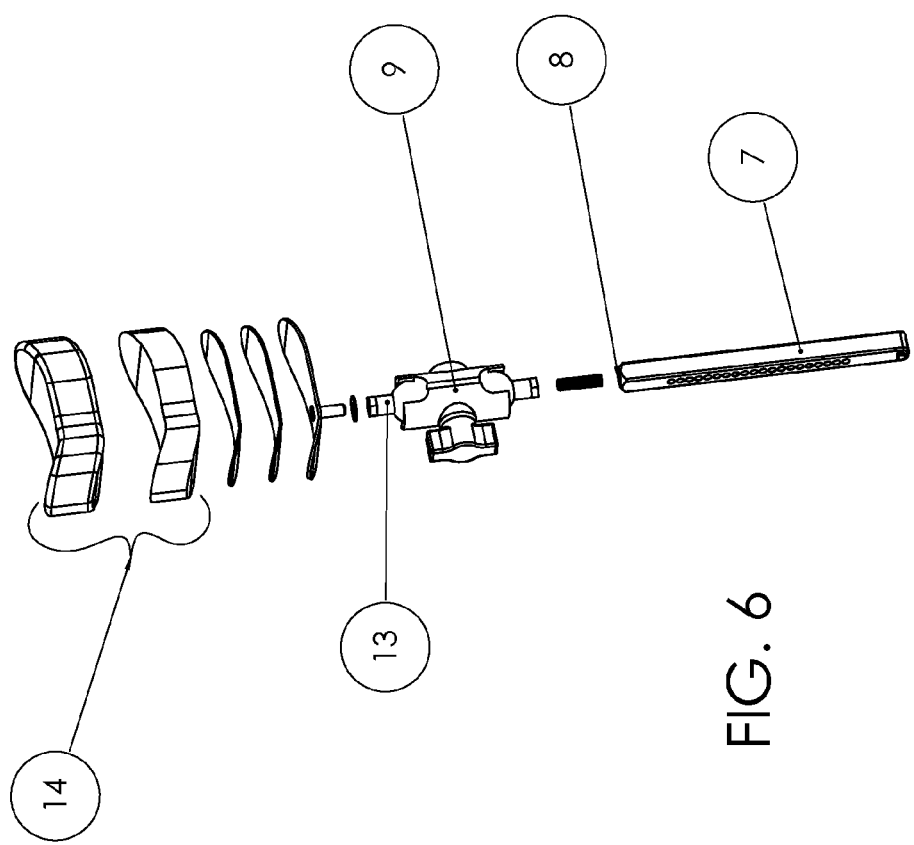
FIG. 6 is an exploded view of the chin support assembly.
Figure 8:
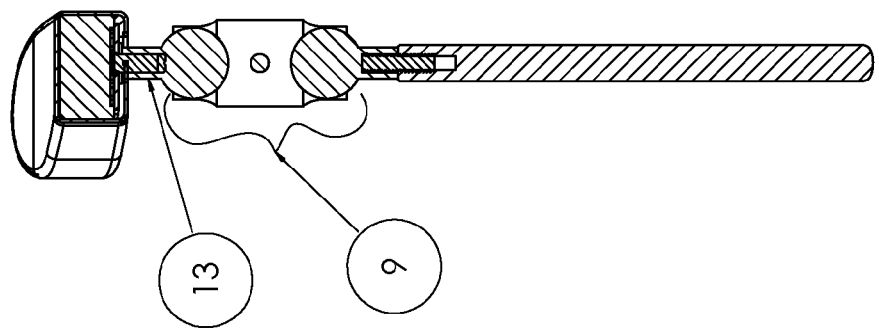
FIG. 8 is a cross-section view of the chin support assembly.
Figure 7:
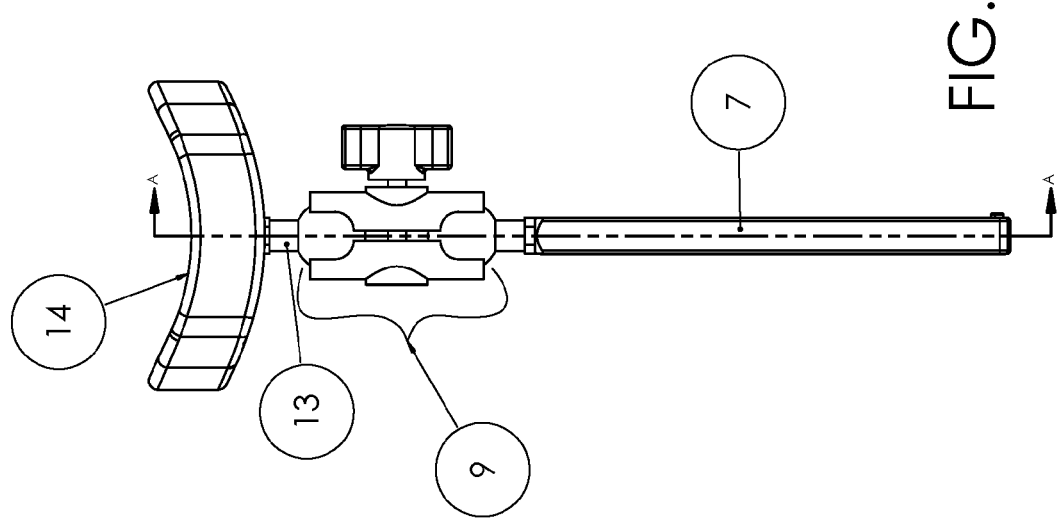
FIG. 7 is a front view of the chin support assembly.
Figure 11:
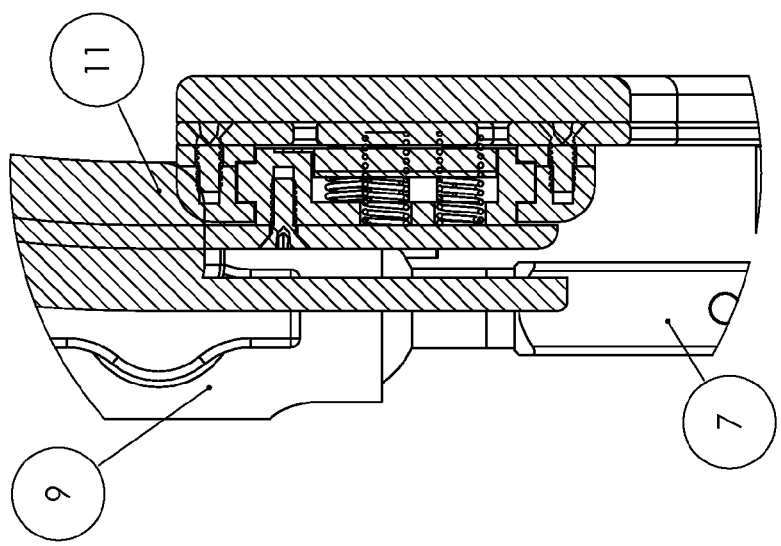
FIG. 11 is a detail view of the brace.
Figure 10:
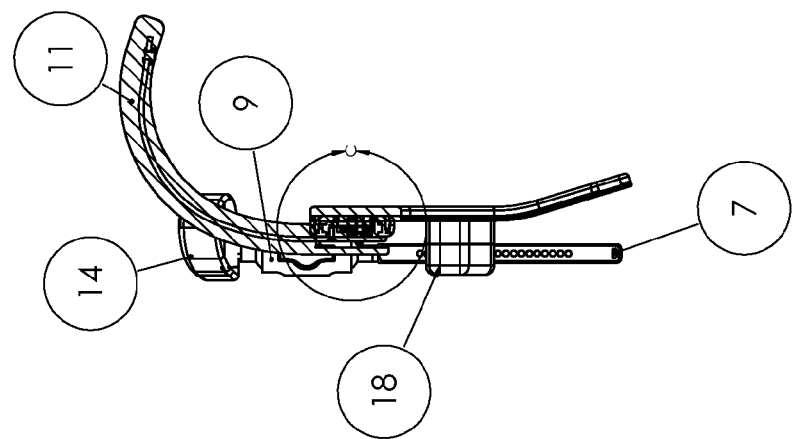
FIG. 10 is a cross-section view of the brace.
Figure 9:
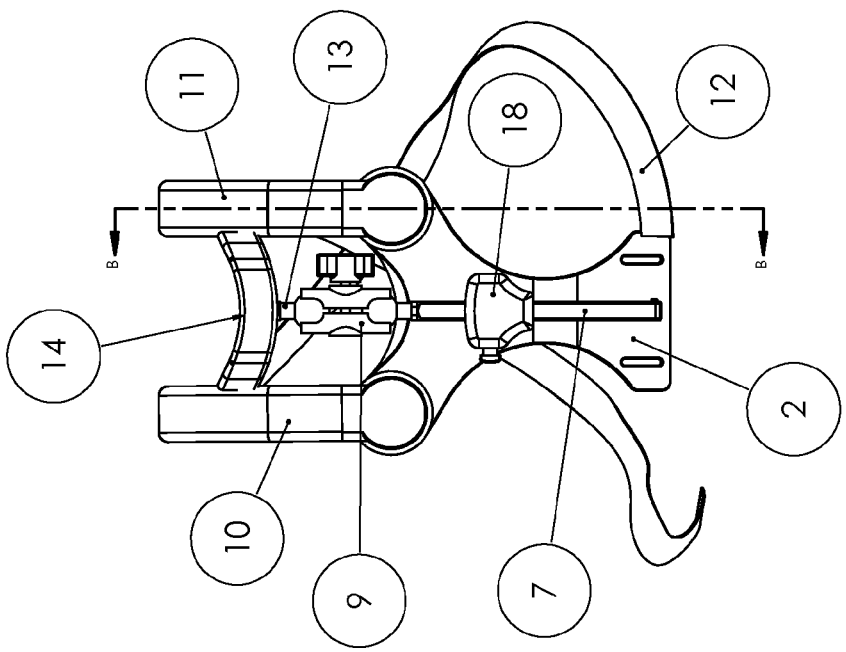
FIG. 9 is a front view of the brace.
Figure 15:
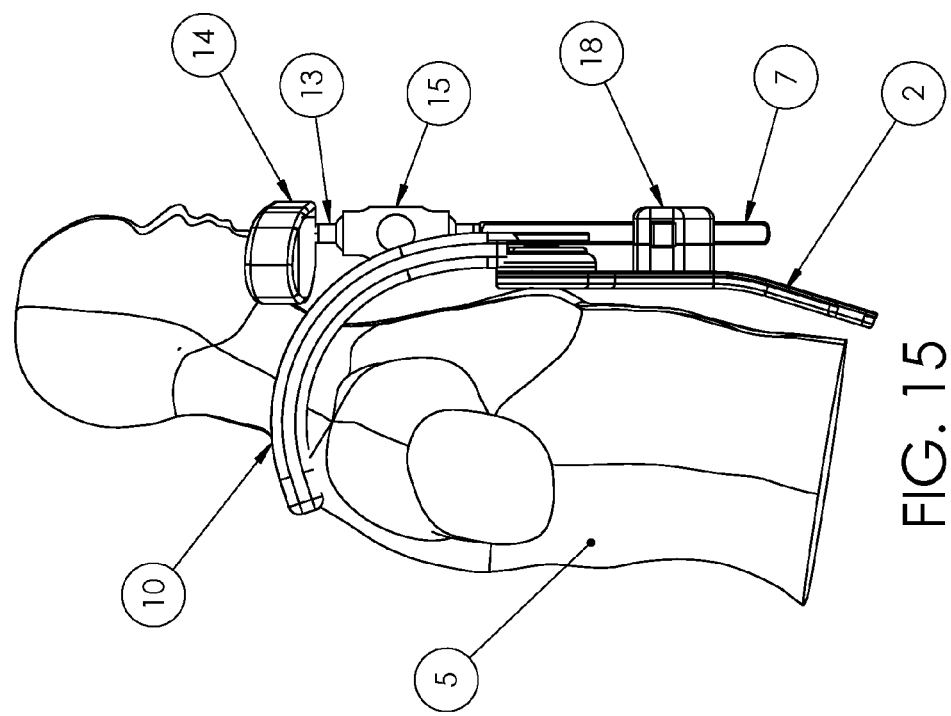
FIG. 15 is a side view of the brace on a patient.
Figure 14:
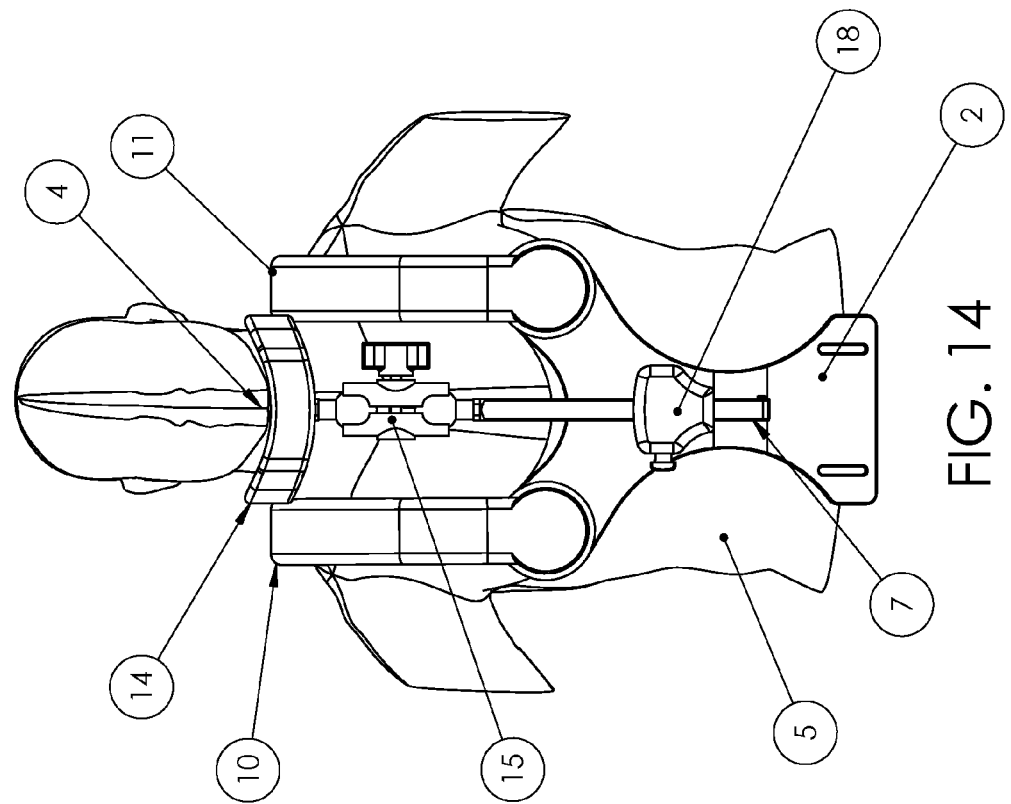
FIG. 14 is a front view of the brace on a patient.
Figure 2:
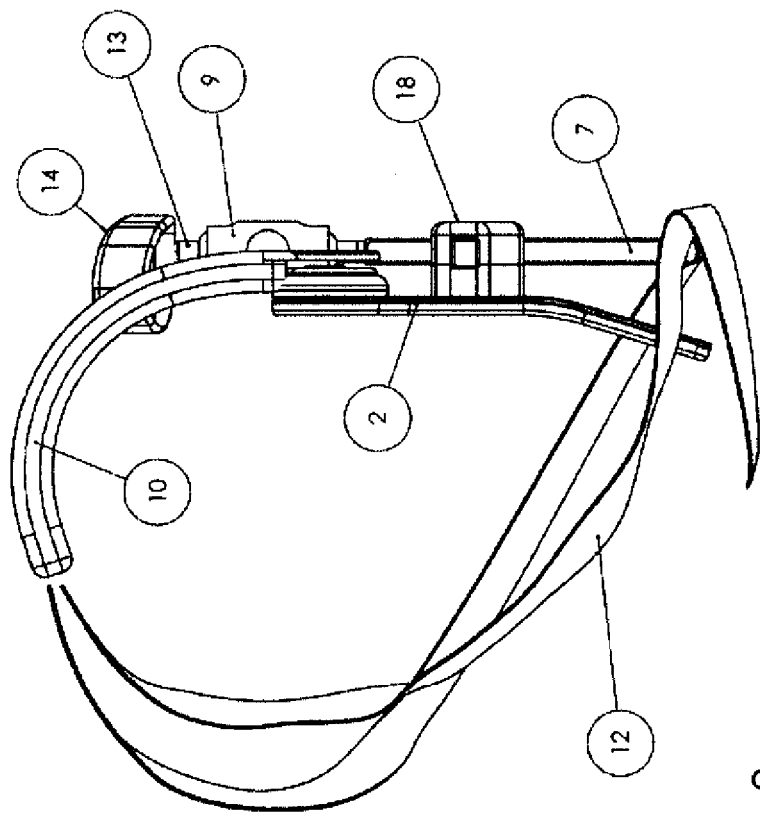
Figure 5:
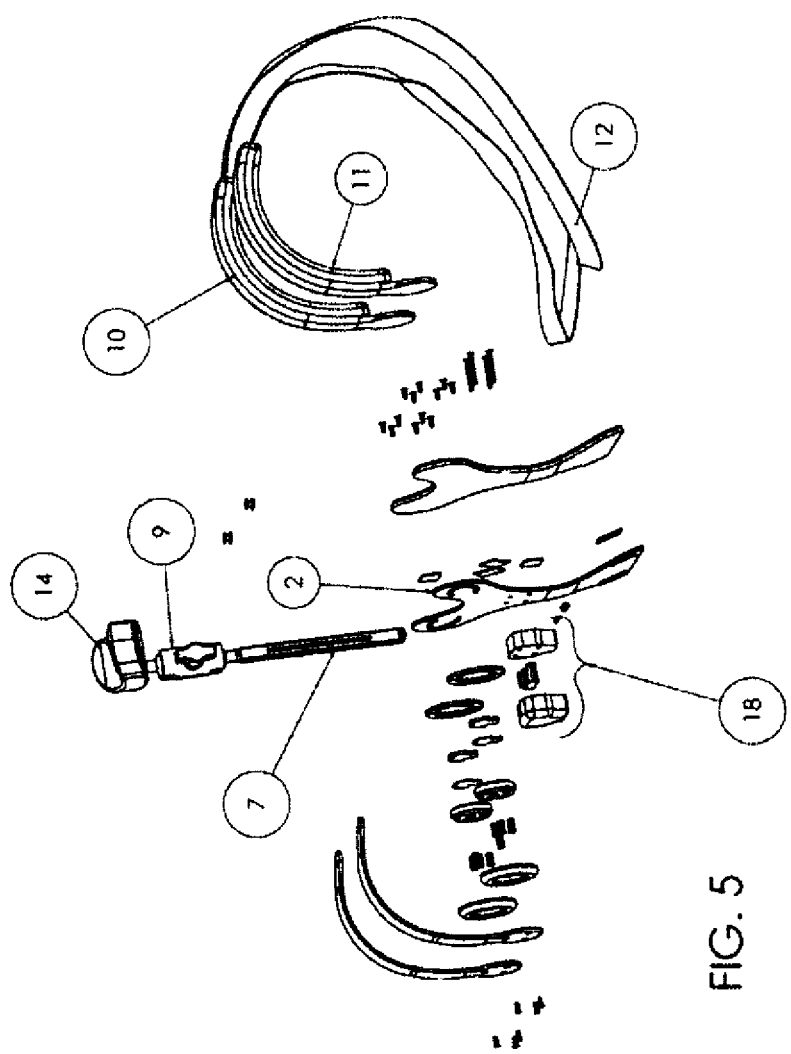
Figure 8:
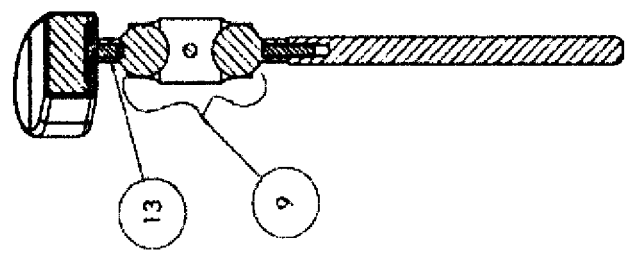
Figure 7:
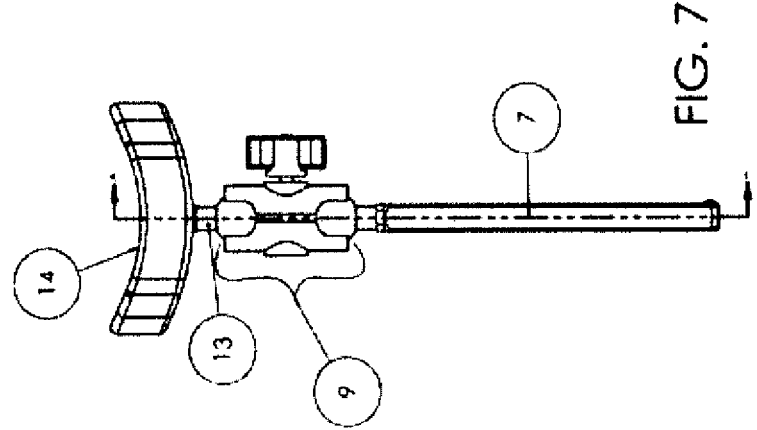
Figure 11:
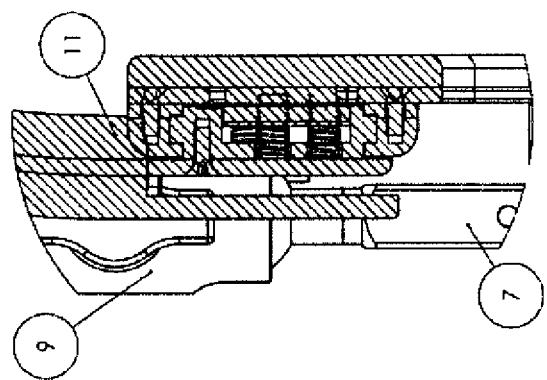
Figure 10:
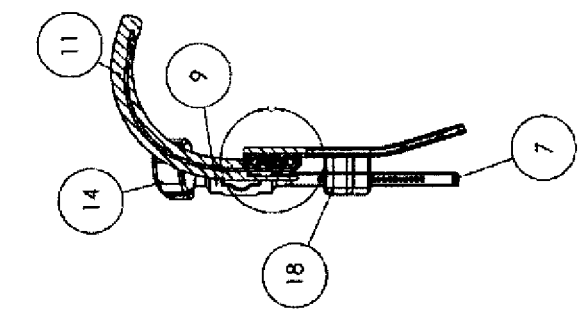
Figure 9:
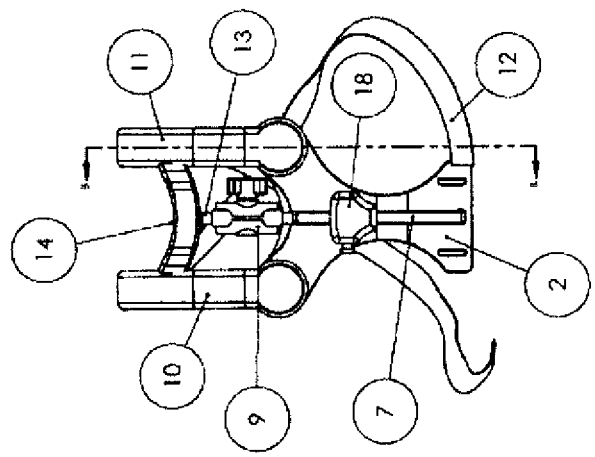

The adjustable linkage 15 connects the chin support to the top surface 8 of the rod 7. The adjustable linkage 15 permits adjustment of the chin support relative to the chest plate 2 and the ability to lock the chin support in a selected position relative to the rod 7. The dual ball joint 15 shown in figure 4 is one such adjustable linkage 15. The dual ball joint 9 includes two curved plates 19 and one locking screw 20. The dual ball joint 9 is completely adjustable before it is fixed in place by the locking mechanism 20 and this allows for aligning the chin rest under the patient's chin in dimensions thus allowing for adaptation to different anatomies and symmetries of different patient's jaws.

In use the chest plate 2 is fastened by means of the left shoulder brace 10, right shoulder brace 11, and adjustable straps 12 to The Patient's chest and the rod 7 is adjusted to place the chin support at a selected height relative to the Patient's chest by an adjustable connector 18 connecting the rod 7 to the chest plate 2. Then the technician places the chin support at a desired location and the Patient's chin 4 is placed in contact with the chin support. The adjustable linkage 15 is then locked and the Patient's chin 4 is thereby immobilized.

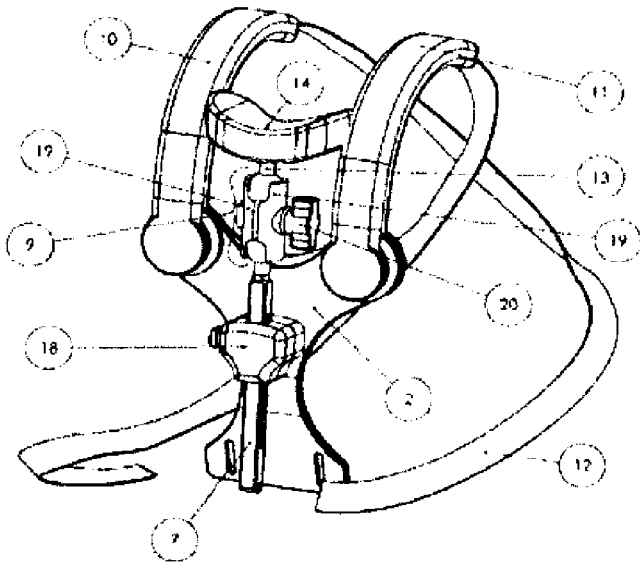

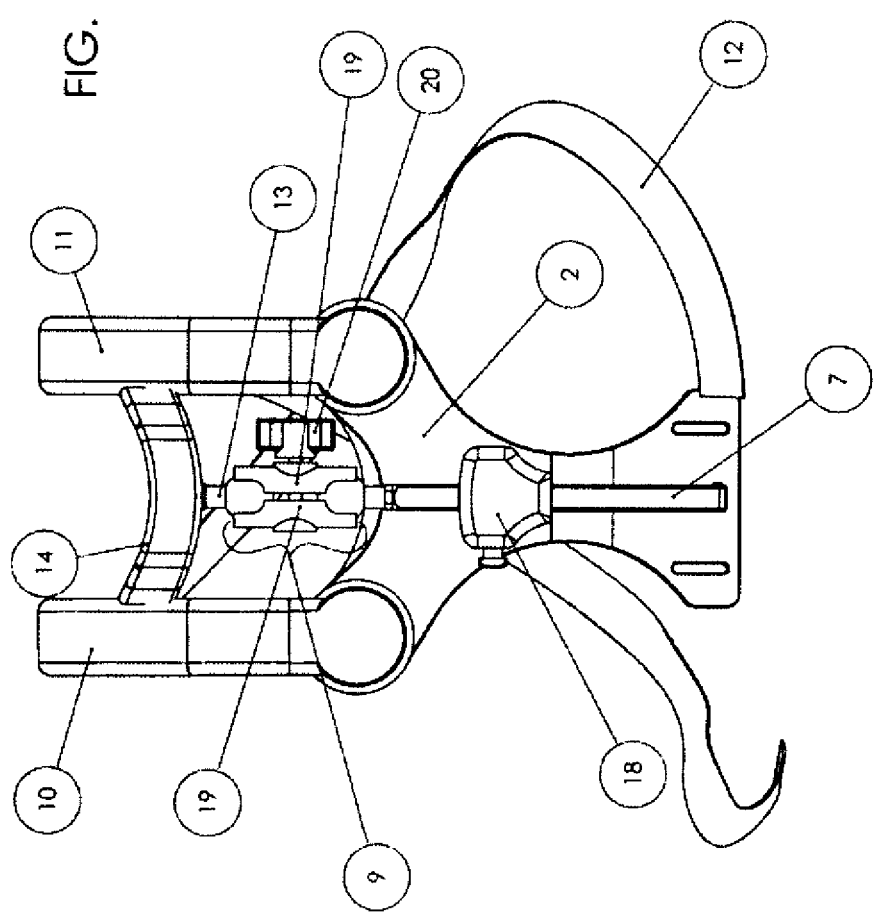

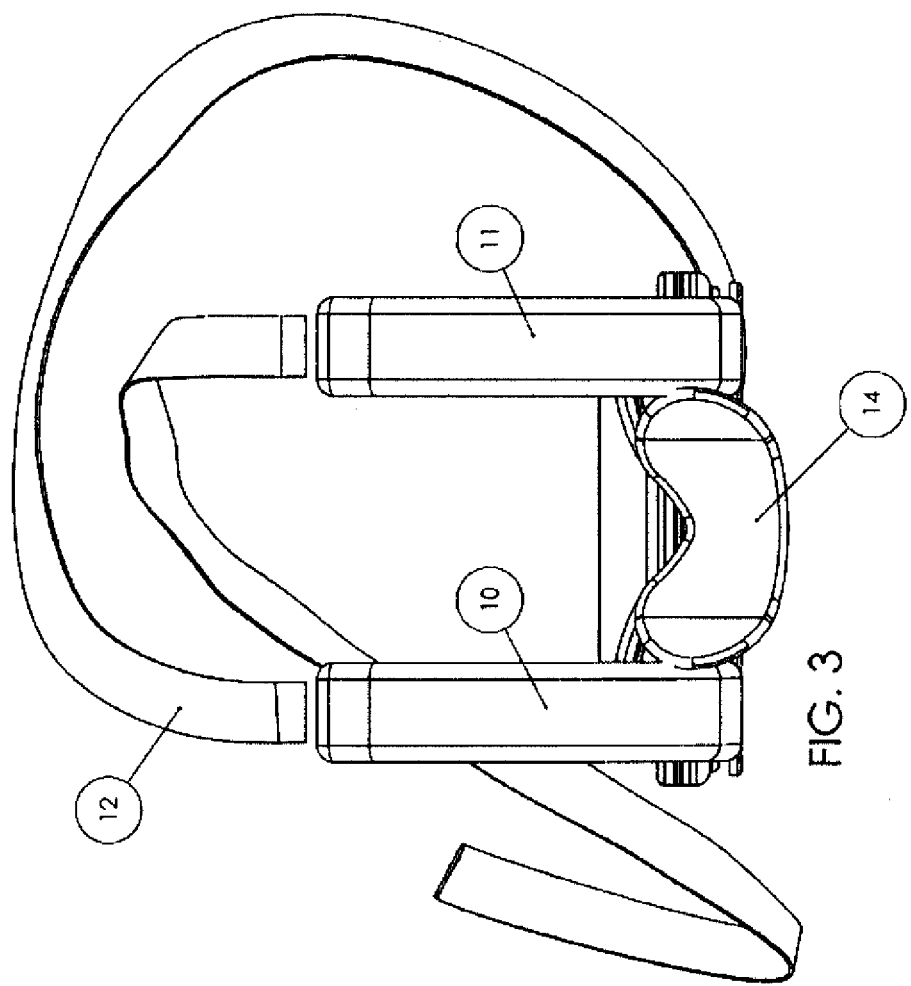

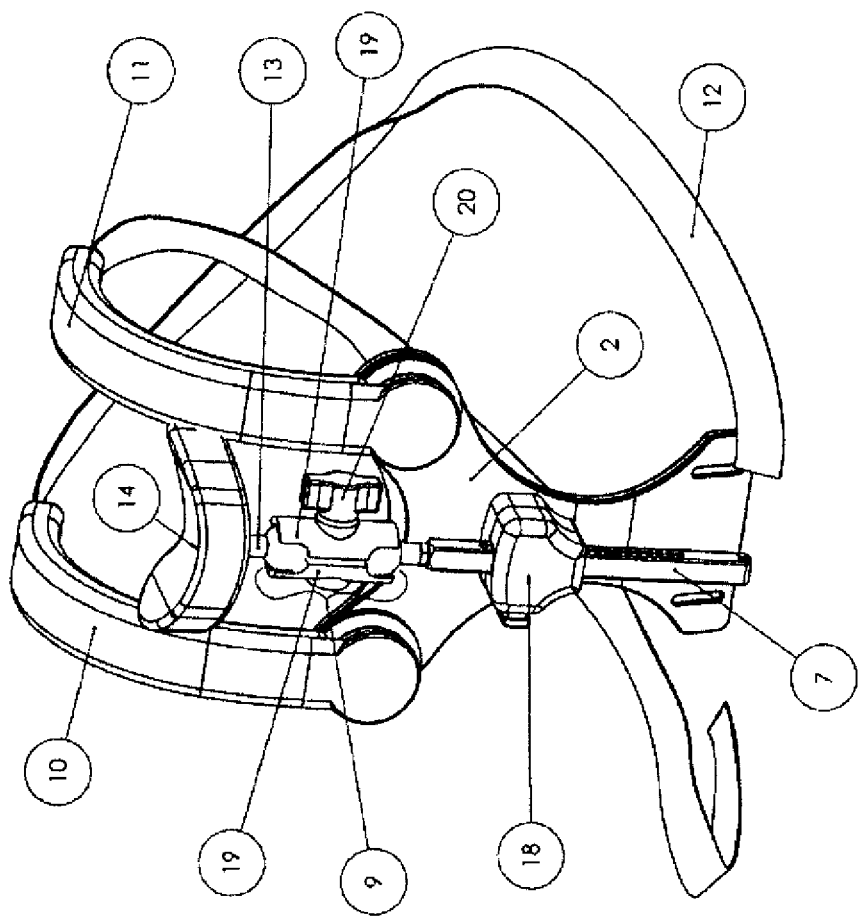

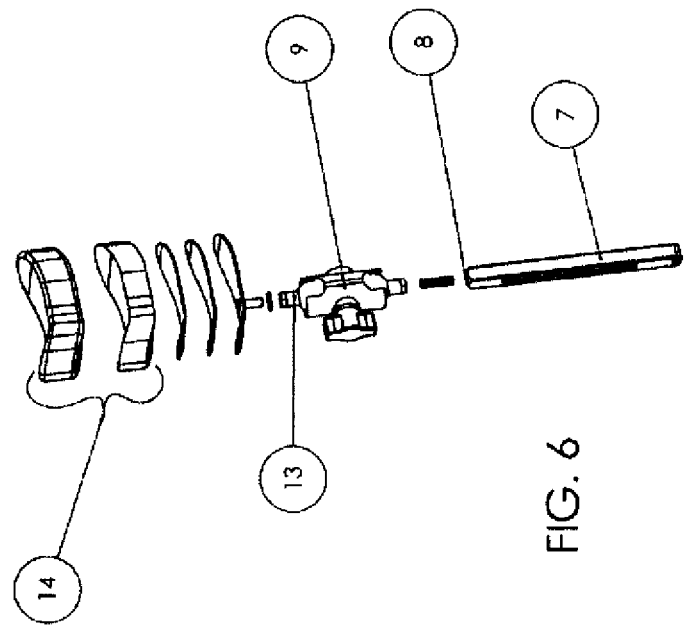

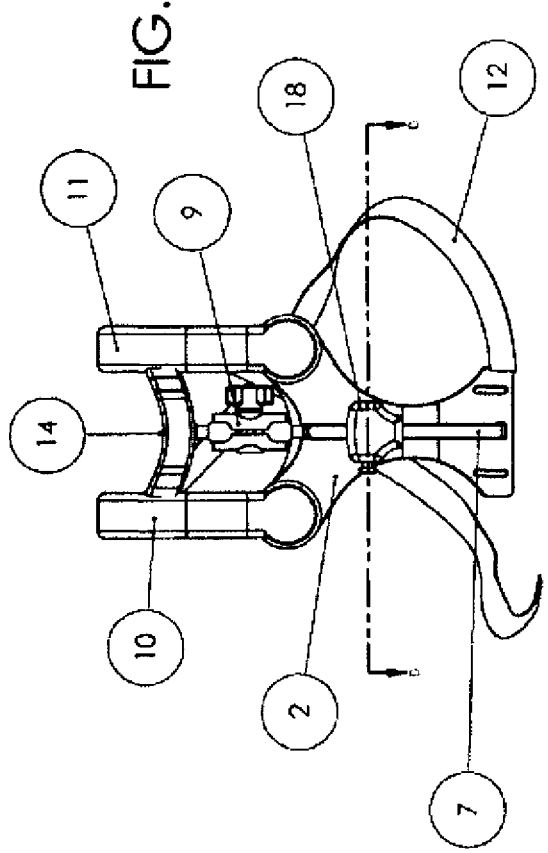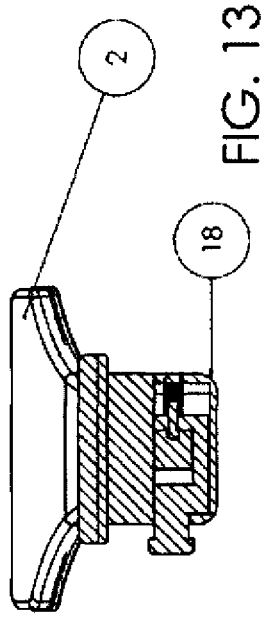

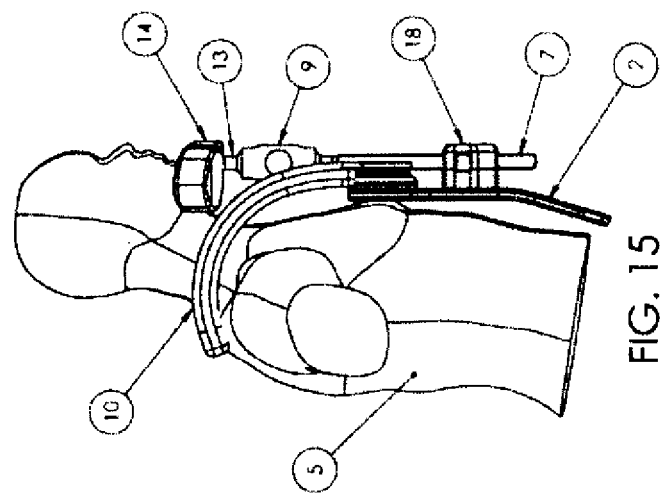
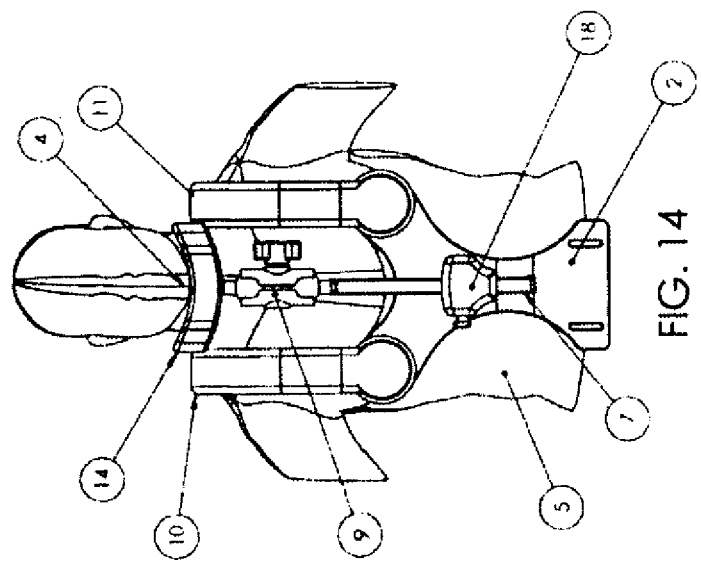

We claim:

1. A brace comprising:
   a) a chest plate;
   b) a chin support for supporting a patient's chin in a fixed position relative to said patient's chest;
   c) a rod having a top surface, said rod adjustably attached to said chest plate; and
   d) an adjustable linkage adjustably connected said top surface to said chin support, wherein said adjustable linkage includes a dual ball joint, said dual ball joint including a locking mechanism comprising a pair of curved plates and a single locking screw.

2. the brace of claim 1 wherein at least two straps are provided to secure the brace to a user's chest.

3. the brace of claim 2 wherein said straps are positioned and sized to cross each other on the patient's posterior side.

4. The brace of claim 1 wherein said dual ball joint lock mechanism further comprises a single handle for compressing said curved plates.

5. The brace of claim 1 further comprising a left shoulder brace connected to said chest plate, and a right shoulder brace connected to said chest plate.

6. The brace of claim 1 wherein said rod is square in cross section.

7. the brace of claim 1 wherein said chin support is kidney shaped.

8. the brace of claim 1 further comprising an adjustable connector slideably attaching said rod to said chest plate.

* * * * *

UNITED STATES PATENT AND TRADEMARK OFFICE
CERTIFICATE OF CORRECTION

Page 1 of 13

PATENT NO. : 8,864,694 B2
APPLICATION NO. : 13/457376
DATED : October 21, 2014
INVENTOR(S) : Eric Schiffman It is certified that error appears in the above-identified patent and that said Letters Patent is hereby corrected as shown below:

Title page, illustrative fig(s). 4 should be deleted and substitute therefore the attached title page consisting of illustrative fig(s). 4.

Title Page, Item (57) Abstract, line 2, should read as follows:
--The brace is used to immobilize a Patient's chin relative to The Patient's spinal column, The Patient's chest, or both when the Patient's chin is placed upon the chin support.--

In the Drawings:

The drawing sheets 1-10 consisting of fig(s). 1-15 should be deleted and substitute therefore the attached pages 6-15 consisting of fig(s). 1-15.

In the Specification:

Column 1, line 26 should read as follows:
--the field of medical and dental...--

Column 1, line 31 should read as follows:
--...known in the art that support...--

Column 1, line 42 should read as follows:
--...known in the art that support...--

Column 1, lines 43-44 should read as follows:
--...heat restraint that is rigidly fixed...--

Signed and Sealed this
Tenth Day of March, 2015

Michelle K. Lee
*Deputy Director of the United States Patent and Trademark Office*

CERTIFICATE OF CORRECTION (continued)
U.S. Pat. No. 8,864,694 B2

Column 1, line 49 should read as follows:
--...provide a brace that can be used...--

Column 1, line 60 should read as follows:
--...spinal column, The Patient's chest, or both...--

Column 2, line 21 should read as follows:
--...linkage connected to said...--

Column 2, line 23 should read as follows:
--...relative to The Patient's chest when...--

Column 2, line 37 should read as follows:
--...adjustable linkage and a pad 14.--

Column 2, line 38 should read as follows:
--...the adjustable linkage includes...--

Column 2, line 42 should read as follows:
--...the chin support by welding or by...--

Column 2, line 46 should read as follows:
--...linkage and is slideably...--

Column 2, line 51 should read as follows:
--...adjustable linkage connects the chin...--

Column 2, line 52 should read as follows:
--...adjustable linkage permits...--

Column 2, line 55 should read as follows:
--...dual ball joint 9 shown in...--

Column 2, line 56 should read as follows:
--...adjustable linkage. The dual ball...--

Column 3, line 3 should read as follows:
--The adjustable linkage is...--

(12) United States Patent
Schiffman et al.

(10) Patent No.: US 8,864,694 B2
(45) Date of Patent: Oct. 21, 2014

(54) BRACE

(76) Inventors: Eric Schiffman, St. Paul, MN (US); Thomas Michael Speidel, Minneapolis, MN (US)

(*) Notice: Subject to any disclaimer, the term of this patent is extended or adjusted under 35 U.S.C. 154(b) by 138 days.

(21) Appl. No.: 13/457,376

(22) Filed: Apr. 26, 2012

(65) Prior Publication Data
US 2013/0289460 A1  Oct. 31, 2013

(51) Int. Cl.
A61F 5/00 (2006.01)

(52) U.S. Cl.
USPC ............................................. 602/18

(58) Field of Classification Search
CPC ........ A61F 5/01; A61F 5/0102; A61F 5/04; A61F 5/055; A61F 5/058; A61F 5/05883; A61G 13/02; A61G 13/12; A61G 13/121; A47C 20/00
USPC ......... 602/5, 16-19, 32; 128/97.1, 103.1, 846, 128/869, 870; 5/621, 622, 637
See application file for complete search history.

(56) References Cited

U.S. PATENT DOCUMENTS

| | | | | |
|---|---|---|---|---|
| 2,223,276 A * | 11/1940 | Ward | | 602/18 |
| 2,735,424 A * | 2/1956 | Benjamin | | 602/17 |
| 2,820,455 A * | 1/1958 | Hall | | 602/18 |
| 2,904,040 A * | 9/1959 | Hale | | 602/18 |
| 4,628,913 A * | 12/1986 | Lerman | | 602/18 |
| 5,201,702 A * | 4/1993 | Mars | | 602/17 |
| 5,208,928 A * | 5/1993 | Kuck et al. | | 5/608 |
| 5,531,669 A * | 7/1996 | Vacanu | | 602/18 |
| 7,789,843 B2 * | 9/2010 | Ray | | 602/18 |
| 8,001,633 B2 * | 8/2011 | Swain, Jr. | | 5/621 |
| 8,057,415 B2 * | 11/2011 | Hipp et al. | | 602/18 |
| 8,529,482 B2 * | 9/2013 | Giontella | | 602/18 |
| 2006/0217648 A1 * | 9/2006 | Rogachevsky | | 602/20 |
| 2009/0187129 A1 * | 7/2009 | Ben-Cialim et al. | | 602/18 |

* cited by examiner

Primary Examiner — Patricia Bianco
Assistant Examiner — Raymond E Harris
(74) Attorney, Agent, or Firm — Roger L. Belfay

(57) ABSTRACT

The brace includes: a chest plate; a chin support; a rod having a top surface, the rod adjustably attached to the chest plate; and an adjustable linkage connected to the top surface and to the chin support. The brace is used to immobilize a Patient's chin relative to The Patient's spinal column, or The Patient's chest, or both when the Patient's chin is placed upon the chin support.

8 Claims, 10 Drawing Sheets

FIG. 4